US00PP32491P3

(12) United States Plant Patent
Beckman

(10) Patent No.: US PP32,491 P3
(45) Date of Patent: Nov. 17, 2020

(54) CALLA LILY PLANT NAMED 'DIVA ALPINA'

(50) Latin Name: *Zantedeschia aethiopica*
Varietal Denomination: Diva Alpina

(71) Applicant: Dümmen Group B.V., De Lier (NL)

(72) Inventor: Peter Beckman, Santa Cruz, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/602,428

(22) Filed: Oct. 2, 2019

(65) Prior Publication Data

US 2020/0113109 P1 Apr. 9, 2020

Related U.S. Application Data

(60) Provisional application No. 62/766,213, filed on Oct. 5, 2018.

(51) Int. Cl.
*A01H 5/02* (2018.01)
*A01H 6/56* (2018.01)

(52) U.S. Cl.
USPC ..... Plt./490
CPC ..... *A01H 6/56* (2018.05)

(58) Field of Classification Search
USPC ..... Plt./490
CPC ..... A01H 5/02
See application file for complete search history.

*Primary Examiner* — Annette H Para
(74) *Attorney, Agent, or Firm* — The Webb Law Firm

(57) ABSTRACT

'Diva Alpina' is a new variety of calla lily plant having white colored spathes. The leaves are green with maculations present.

1 Drawing Sheet

Botanical classification: *Zantedeschia aethiopica.*
Varietal denomination: 'Diva Alpina'.

BACKGROUND OF THE NEW PLANT

The present invention comprises a new and distinct cultivar of calla lily, botanically known as *Zantedeschia aethiopica* and hereinafter referred to by the cultivar name 'Diva Alpina'.

'Diva Alpina' is a product of a planned breeding program and the new cultivar was selected in Santa Cruz, Calif. from the F2 population of the crossing of unpatented *Zantedeschia* seedling 7029-23 (female parent) with unpatented *Zantedeschia* seedling 95109 (male parent). When compared to its female parent, the leaves of 'Diva Alpina' are smaller, lanceolate in shape, and with smaller maculations. Further, its blooms are smaller, more abundant, and appear earlier. The leaf maculations of 'Diva Alpina' are one distinguishing characteristic from its male parent that exhibits no maculations.

The new variety was initially asexually reproduced through tissue culture propagation in Santa Cruz, Calif. Asexual reproductions of 'Diva Alpina' have demonstrated that the combination of characteristics as herein disclosed for the new variety are retained and reproduced true to type through successive generations of asexual reproduction.

Color references are made to The 2001 R.H.S. Colour Chart of The Royal Horticultural Society of London, 4$^{th}$ Edition, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Diva Alpina' which, in combination, distinguish this calla lily as a new and distinct cultivar:

1. White colored spathes;
2. Very early bloom time; and
3. Leaf maculations present.

Table 1 provides a comparison of 'Diva Alpina' to similar *Zantedeschia aethiopica* varieties 'A405' (U.S. plant patent pending) and 'Colombe de la Paix' (unpatented). Further, depending on temperature, light, and initial plant size, the forcing time of 'Diva Alpina' is 2 weeks shorter than 'Colombe de la Paix'.

TABLE 1

| Comparison variety | Differing trait(s) | Comparison expression | Present variety expression |
|---|---|---|---|
| 'A405' | Plant height | 30-40 cm | 35-50 cm |
| 'Colombe de la Paix' | Plant height | 60-150 cm | 35-50 cm |
| | Leaf maculations | None present | Present |

BRIEF DESCRIPTION OF THE DRAWING

The accompanying photographic drawing illustrates the new variety, with the colors being as nearly true as is possible with color illustrations of this type.

DESCRIPTION OF THE NEW PLANT

Type: Evergreen.
Form: Semi-spreading.
Height of leaf canopy above the soil: 35-50 cm.
Height of top of inflorescences above the soil: 55-75 cm.
Number of inflorescences per tuber:

14-16 *cm in diameter*.—3-5.
18-20 *cm in diameter*.—4-6.
20-22 *cm in diameter*.—5-10.

Lastingness of inflorescences on the plant: 14-21 days.

Main use: Potted plant.

Disease/pest resistance: Very strong tolerance to *Pythium* root rot and other root pathogens.

Root color: White.

Berries: None present.

Leaves:

*Width*.—4-8 cm.
*Length*.—13-25 cm.
*Shape*.—Lanceolate to ovate and slightly sagittate at the base.
*Apex*.—Apiculate.
*Base*.—Sagittate.
*Margin*.—Entire.
*Color*.—Upper surface: Green Group RHS 137A, with moderately dense, evenly distributed White Group RHS 155C to 155D maculations present. Lower surface: Green Group RHS 137B, with moderately dense, evenly distributed White Group RHS 155C to 155D maculations present.
*Surface texture*.—Smooth (both surfaces).
*Leaf venation*.—None/indistinct.
*Petiole*.—Length: 25-45 cm. Diameter: 0.4-0.75 cm. Texture: Smooth. Shape: Very slim columnar. Color: The base and upper portion are Green Group RHS 137B.

Spathe:

*Length*.—9-13 cm.
*Width*.—6.5-8 cm.
*Height*.—9-13 cm.
*Fragrance*.—Slightly sweet.
*Shape*.—Funnel, with an open back.
*Texture*.—Smooth.
*Apex*.—Pointed.
*Base*.—Continuous.
*Margin*.—Entire.
*Throat spot*.—Absent.
*Color*.—White Group RHS 155D (upper and lower surfaces).

Spadix:

*Length*.—3-6 cm.
*Diameter*.—0.3-0.6 cm.
*Color*.—Yellow Group RHS 13A to 13B.
*Position relative to spathe*.—Upright from base.
*Apex*.—Apiculate.
*Location of female organs*.—Upper portion of spadix.
*Location of male organs*.—Lower portion of spadix.
*Pistil number*.—Numerous, more than 20.
*Pollen color*.—White Group RHS 155A to 155B.

Peduncle color: Green Group RHS 137A to Yellow-Green Group RHS 144A.

I claim:

1. A new and distinct variety of calla lily plant named 'Diva Alpina' as herein described and illustrated.

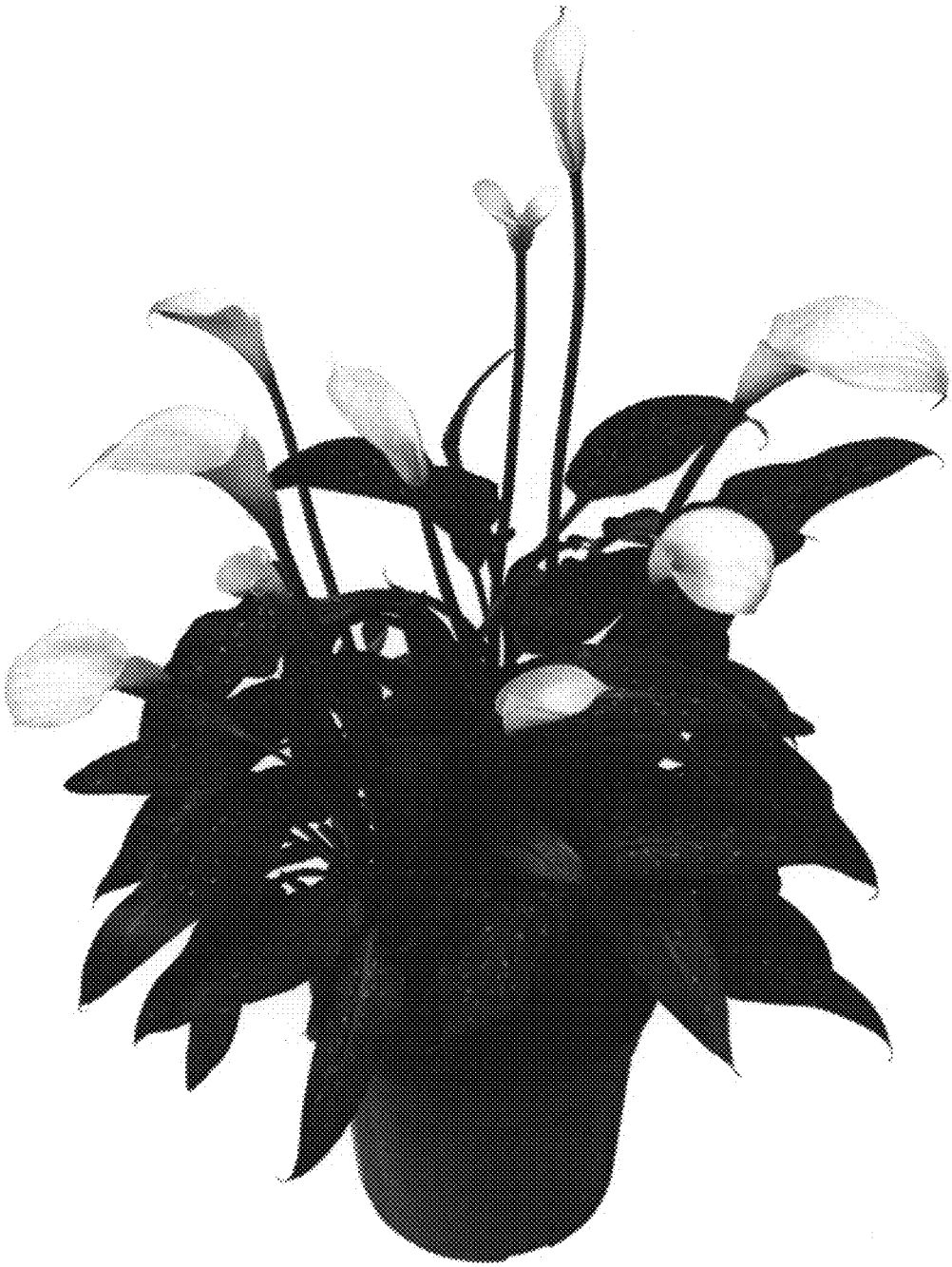

* * * * *